(12) United States Patent
Wang et al.

(10) Patent No.: US 8,058,602 B2
(45) Date of Patent: Nov. 15, 2011

(54) LONG-LENGTH INDUSTRY CAMERA IMAGE SENSOR FOR FLAT SURFACE INSPECTION APPLICATION

(75) Inventors: Weng-Lyang Wang, Saratoga, CA (US); Shengmin Lin, Santa Clara, CA (US); Chi-Pin Lin, Kaohsiung (KR); Feng Ke Hsiao, Nantou (TW)

(73) Assignee: CMOS Sensor, Inc., Cupertino, CA (US)

( * ) Notice: Subject to any disclaimer, the term of this patent is extended or adjusted under 35 U.S.C. 154(b) by 257 days.

(21) Appl. No.: 12/392,102

(22) Filed: Feb. 25, 2009

(65) Prior Publication Data

US 2010/0213355 A1 Aug. 26, 2010

(51) Int. Cl.
*H01L 27/00* (2006.01)

(52) U.S. Cl. ........................ 250/208.1; 250/239

(58) Field of Classification Search ........... 250/208.1, 250/239, 216; 358/484, 471–475, 494–497, 358/462, 446, 513–518
See application file for complete search history.

(56) References Cited

U.S. PATENT DOCUMENTS

| | | | | |
|---|---|---|---|---|
| 4,783,700 A | * | 11/1988 | Nagane | 358/482 |
| 5,038,027 A | * | 8/1991 | Ioka | 250/208.1 |

* cited by examiner

*Primary Examiner* — Que T Le
(74) *Attorney, Agent, or Firm* — CH Emily LLC; Chein-Hwa Tsao (57) ABSTRACT

A long-length industry camera image sensor (LICIS) is proposed for, expressed in X-Y-Z coordinates, converting a pixel line image (PLI) of length $L_{PL}$ along X-direction into a line image signal (LIS). The LICIS includes a full-width linear image sensor (FLIS) of length $L_{IS}$ along X-direction and displaced from the PLI along Z-direction by an imaging distance $D_{IMG}$ for converting an incident line image (ILI) impinging upon its FLIS top surface into the LIS. Where $L_{IS}$ is about equal to $L_{PL}$. The LICIS also has a full-width linear rod lens (FLRL) of length $L_{RL}$ along X-direction and displaced from the PLI in Z-direction by a working distance $D_{WKG}$. Where $L_{RL}$ is about equal to $L_{PL}$ and $D_{WKG}$ is selected such that the PLI gets focused by the FLRL into the ILI at the FLIS top surface with an imaging magnification factor of about 1:1.

9 Claims, 10 Drawing Sheets

Fig. 1 Present Invention

Fig. 2 Present Invention

Fig. 3A Present Invention

Fig. 3B Present Invention

Fig. 3C Present Invention
View A-A

Fig. 4A Present Invention

Fig. 4B Present Invention

Fig. 5A

LONG-LENGTH INDUSTRY CAMERA IMAGE SENSOR FOR FLAT SURFACE INSPECTION APPLICATION

BACKGROUND OF THE INVENTION

1. Field of the Invention

The present invention relates to electronic imaging. More particularly, the present invention is related to an I-CIS (Industrial Camera Image Scanner) such as used for large flat panel inspection.

2. Related Background Art

A prior art camera image scanner configuration for industrial application is illustrated in FIG. A. Such industrial application includes, for example, the real-time inspection of large liquid crystal display (LCD) production panels, thin film solar panels and textile production webs. Here, an object surface located in an object plane is, while being illuminated by an Illumination Source, imaged by a charge coupled device (CCD) Image Sensor located at an "Imaging Distance" away from the object plane (along Z-direction). While not specifically illustrated here, to those skilled in the art a real inspection of the object surface can be accomplished by imaging the object surface on a scan-line by scan-line basis, with each scan line width labeled "Object Image Width" (X-direction), while providing a controlled relative motion (along Y-direction) between the object surface and the CCD Image Sensor. In an industrial application, the Object Image Width can be easily as large as 36" to 72". As the "Image sensor Width" of a single CCD Image Sensor is only in the range of 1" to 2" that is substantially smaller than the Object Image Width, an intervening focusing optical path with a Focusing Lens effecting a tiny magnification factor (1:72 to 1:18) is required between the object plane and the imaging surface of the CCD Image Sensor. Given the large Object Image Width and tiny magnification factor, the resulting Imaging Distance lies typically in the range of 10-30 cm.

FIG. B is a basic lens ray diagram for the focusing optical path of the prior art camera image scanner configuration of FIG. A. In addition to a Normal Imaging Light Ray along the Z-axis, a large number of Oblique Imaging Light Rays, each at an Oblique Angle θ from the Normal Imaging Light Ray, need to be focused between the CCD Imaging surface and the Object Plane as well. As the Oblique Angle θ becomes progressively larger toward the edge of the object plane, in the absence of any so-called f-θ compensation in the Focusing Lens design the Oblique Imaging Light Rays would become progressively out of focus as illustrated by the dashed arc tangential to the object plane. Given the imaging geometric parameters involved the Oblique Angle θ can become as large as 60 to 70 degrees where the degree of f-θ compensation can become unacceptable even with an expensive f-θ Focusing Lens. Additionally, it is known in the art that the imaging light intensity falls off toward the edge of the object plane following the cosine-law below:

$$\text{Intensity}(\theta) = I_0 \times \cos^4(\theta)$$

Where $I_0$ is the imaging light intensity at θ=0 degree. Thus, for example, at θ=60 degree Intensity (60 degree)=6.25%×$I_0$. Such a loss of imaging light intensity near the edge of the object plane is most likely unacceptable in that its associated image signal level and signal-to-noise ratio (S/N) would be too low.

FIG. C illustrates another prior art wherein multiple line cameras (Camera-1, Camera-2, Camera-3, etc.) are juxtaposed with a camera pitch along the object image width for large flat panel inspection. Thus, for each camera, the magnification factor is proportionally increased while the Oblique Angle α, is proportionally reduced with the total number of cameras. With the reduction of Oblique Angle α, the problems of f-α compensation and image signal level fall-off at the edges are correspondingly reduced. However, accompanying the increasing number of cameras are disadvantages of bigger overall camera image scanner size, complication of required precision inter camera alignment for image stitching and inter camera imaging parallax error.

Accordingly, it is a primary object of the present invention to provide an Industrial Camera Image Scanner that is compact, having a short Imaging Distance and requiring only simple intervening focusing optical path and simple imaging signal processing.

SUMMARY OF THE INVENTION

A long-length industry camera image sensor (LICIS) is proposed for, expressed in an X-Y-Z Cartesian coordinate system, converting a pixel line image (PLI) of length $L_{PL}$ along the X-direction into a corresponding line image signal (LIS). The LICIS includes:

a) A full-width linear image sensor (FLIS) of length $L_{IS}$ along the X-direction and displaced from the PLI along the Z-direction by an imaging distance $D_{IMG}$ for converting an incident line image (ILI) impinging upon its FLIS top surface into the LIS. Where $L_{IS}$ is about equal to $L_{PL}$.

b) A full-width linear rod lens (FLRL) of length $L_{RL}$ along the X-direction and displaced from the PLI in the Z-direction by a working distance $D_{WKG}$ with $D_{WKG} < D_{IMG}$. Therefore the FLRL is located between the PLI and the FLIS. Where $L_{RL}$ is about equal to $L_{PL}$ and $D_{WKG}$ is selected with respect to $D_{IMG}$ such that the PLI gets focused by the FLRL into the ILI at the FLIS top surface with an imaging magnification factor of about 1:1. In a more specific embodiment, the imaging magnification factor is set to be from about 0.8:1 to about 1.2:1.

In a more specific embodiment, the FLIS includes a multi-segment stitched sensor base board (SSBB) having numerous linearly stitched sensor board segments $SBS_j$, j=(1, 2, ..., M) where M>=1. Each $SBS_j$ converts an incident line image segment ($ILI_j$) of the ILI into a corresponding line image signal segment ($LIS_j$) of the LIS.

In a more specific embodiment, each $SBS_j$ further includes:

A base board ($BB_j$).

Numerous linearly stitched linear sensor integrated circuit $LSIC_{jk}$, k=(1, 2, ..., N) located atop the base board where N>=1. Each $LSIC_{jk}$ converts an incident line image segment ($ILI_{jk}$) of the $ILI_j$ into a corresponding line image signal segment ($LIS_{jk}$) of the $LIS_j$. In one embodiment, each $LSIC_{jk}$ is made of a linear CMOS sensor integrated circuit.

In a more detailed embodiment, each $BB_j$ further includes, along the X-direction, a left-end anti-bumping profile and a right-end anti-bumping profile. The left-end anti-bumping profiles and the right-end anti-bumping profiles are shaped and sized such that, when the $BB_j$ and $BB_{j+1}$ are stitched together, the right-end anti-bumping profile of $BB_j$ will engage the left-end anti-bumping profile of $BB_{j+1}$ and accordingly guaranteeing the following:

A minimum X-direction inter-IC clearance ($IIC_X$) between $LSIC_{jN}$ and $LSIC_{j+1,1}$.

A maximum Y-direction inter-IC offset ($IIO_Y$) between $LSIC_{jN}$ and $LSIC_{j+1,1}$.

In a more specific embodiment, the $IIC_X$ is from about 10 micron to about 30 micron while the $IIO_Y$ is from about 0 micron to about 30 micron.

In a more detailed embodiment, for enclosing the FLIS and the FLRL while affixing them with respect to each other, the LICIS further includes a structured housing having:

A housing base lying in the X-Y plane for seating the FLIS.

Two housing side walls plus a top cover running along the X-axis for enclosing the FLIS and the FLRL. The top cover has a transparent central portion for passing through imaging lights near an optical imaging axis along the Z-direction and reaching the FLRL.

In an important embodiment:

The width of the top cover along the Y-direction is, while avoiding significant blockage of the imaging lights through it, minimized to become narrower than a corresponding width of the housing base.

Correspondingly, the upper portions of both housing side walls are tapered from the housing base toward the top cover so as to minimize the blockage of lateral illumination lights originated near the housing base and aiming at a reflective surface being imaged above the LICIS.

These aspects of the present invention and their numerous embodiments are further made apparent, in the remainder of the present description, to those of ordinary skill in the art.

BRIEF DESCRIPTION OF THE DRAWINGS

In order to more fully describe numerous embodiments of the present invention, reference is made to the accompanying drawings. However, these drawings are not to be considered limitations in the scope of the invention, but are merely illustrative.

FIG. A illustrates a prior art camera image scanner configuration for industrial application having a tiny magnification factor between its object plane and the imaging surface of its CCD Image Sensor.

FIG. B is a basic lens ray diagram for the focusing optical path of the prior art camera image scanner configuration of FIG. A.

FIG. C illustrates another prior art where multiple line cameras are juxtaposed with a camera pitch along the object image width for large flat panel inspection.

DETAILED DESCRIPTION OF THE PREFERRED EMBODIMENTS

The description above and below plus the drawings contained herein merely focus on one or more currently preferred embodiments of the present invention and also describe some exemplary optional features and/or alternative embodiments. The description and drawings are presented for the purpose of illustration and, as such, are not limitations of the present invention. Thus, those of ordinary skill in the art would readily recognize variations, modifications, and alternatives. Such variations, modifications and alternatives should be understood to be also within the scope of the present invention.

Figure 1:
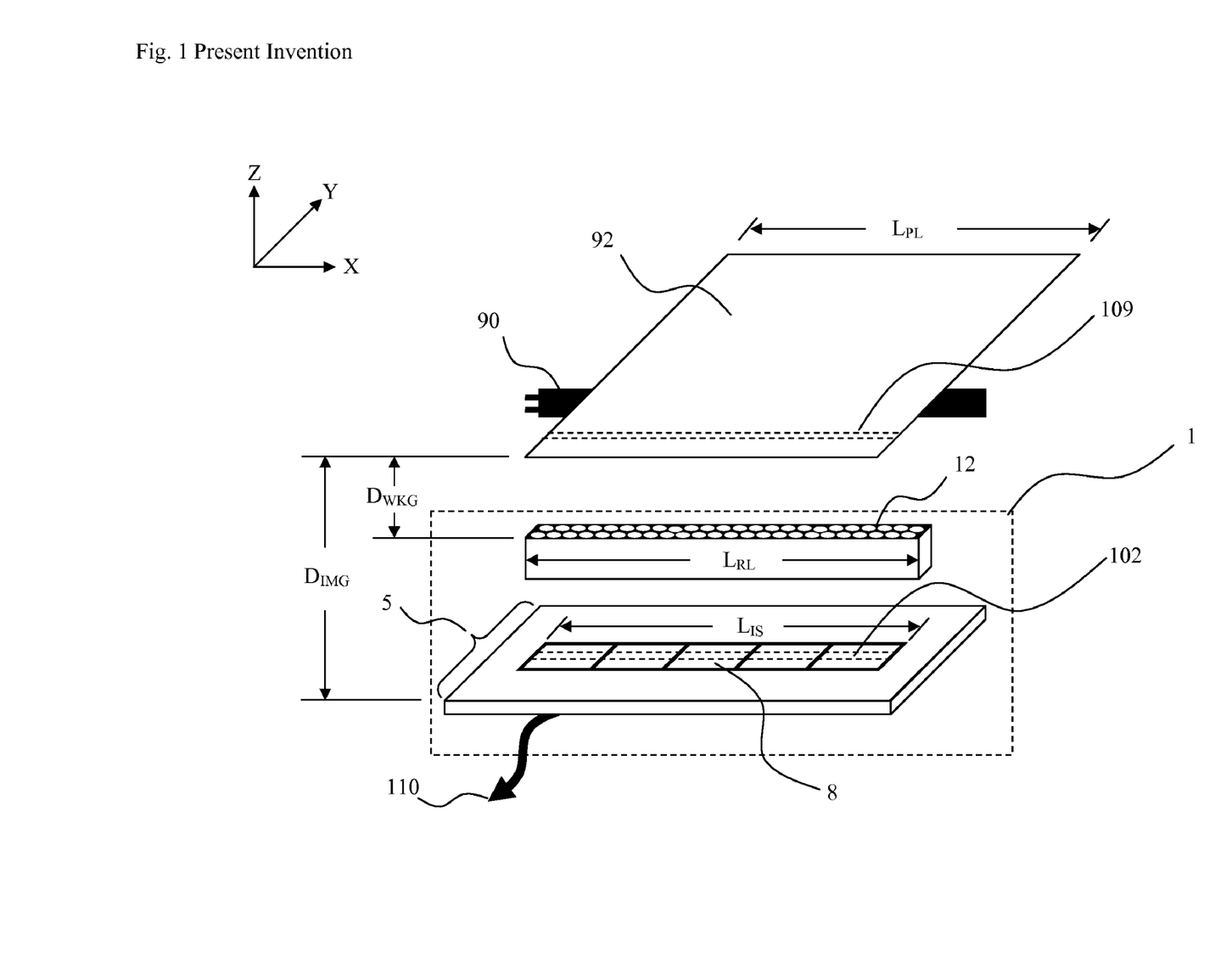
FIG. 1 illustrates the present invention long-length industry camera image sensor (LICIS) using a magnification factor around 1:1 between its object plane and the top imaging surface of its full-width linear image sensor (FLIS)

FIG. 1 illustrates the present invention long-length industry camera image sensor (LICIS) 1 for converting a pixel line image (PLI) 109 of length $L_{PL}$ along the X-direction into a corresponding line image signal (LIS) 110. The pixel line image (PLI) 109 is part of an object plane 92 made visible by an illumination source 90 located nearby and oriented along the X-direction.

The LICIS 1 has a full-width linear image sensor (FLIS) 5 of length $L_{IS}$ along the X-direction and displaced from the pixel line image (PLI) 109 along the Z-direction by an imaging distance $D_{IMG}$ for converting an incident line image (ILI) 102 impinging upon its FLIS top surface 8 into the line image signal (LIS) 110. The LICIS 1 also has a full-width linear rod lens (FLRL) 12 of length $L_{RL}$ along the X-direction and displaced from the pixel line image (PLI) 109 in the Z-direction by a working distance $D_{WKG}$ with $D_{WKG} < D_{IMG}$. The FLRL 12 is therefore located between the pixel line image (PLI) 109 and the FLIS 5. Notably, length $L_{RL}$ is selected to be about equal to length $L_{PL}$ and the working distance $D_{WKG}$ is correspondingly selected with respect to $D_{IMG}$ such that the pixel line image (PLI) 109 gets focused by the FLRL 12 into the incident line image (ILI) 102 at the FLIS top surface 8 with an imaging magnification factor of about 1:1. As a reference, the imaging magnification factor is defined to be:

$$\text{imaging magnification factor} = L_{IS}/L_{PL}$$

In a more specific embodiment, the imaging magnification is set to be from about 0.8:1 to about 1.2:1.

Figure 2:
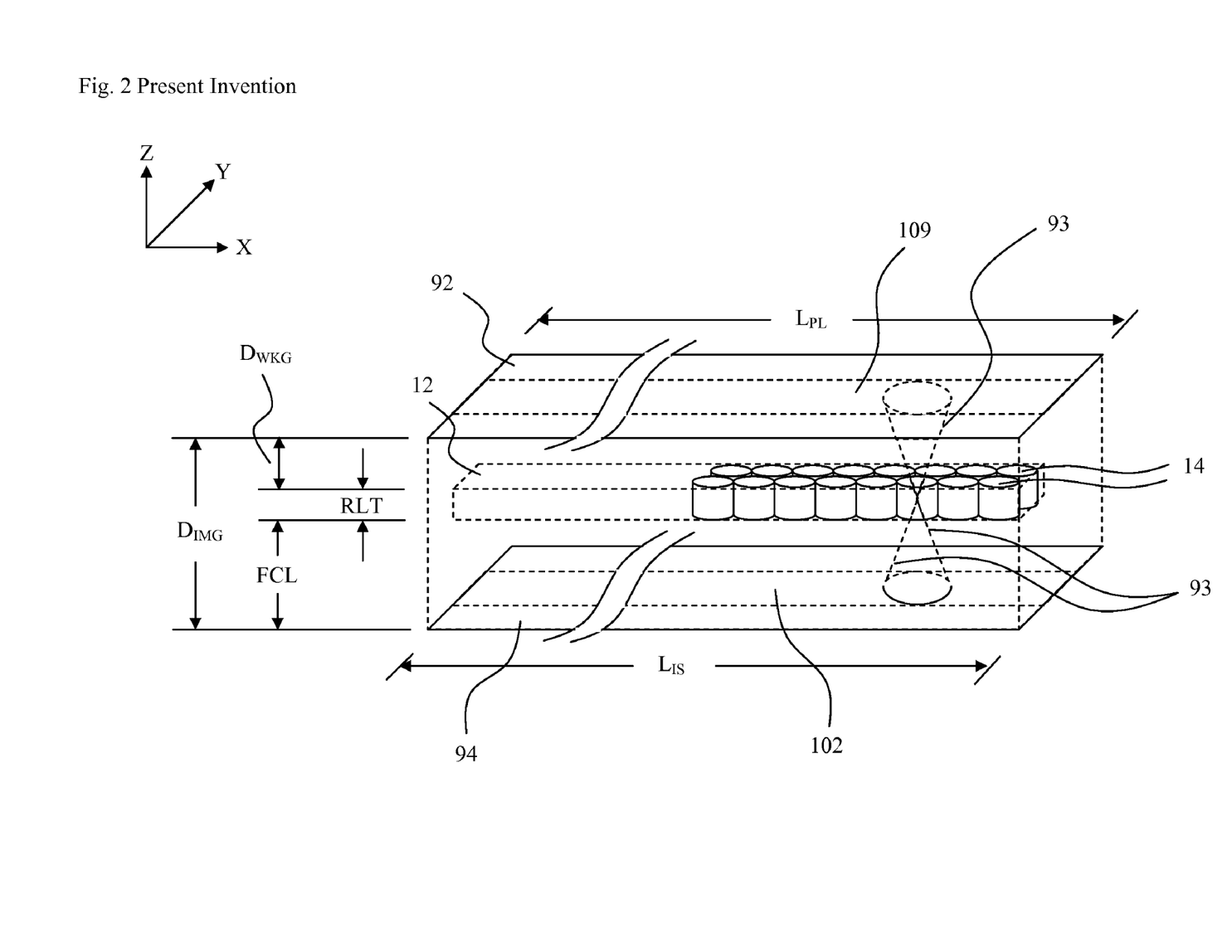
FIG. 2 illustrates the focusing optical path of the present invention long-length industry camera image sensor (LICIS) with a full-width linear rod lens (FLRL) effecting a magnification factor of around 1:1.

FIG. 2 illustrates the focusing optical path 93 of the present invention LICIS 1 with the FLRL 12 effecting a magnification factor of about 1:1. Thus the FLRL 12, being a critical functional part along the focusing optical path 93, focuses the pixel line image (PLI) 109 on the object plane 92 into the incident line image (ILI) 102 on the image plane 94. In one embodiment, as illustrated, the FLRL 12 is made up of an array of rod lenslets 14 along the X-direction and each rod lenslet 14 is a GRIN (gradient index) lens. In practice, for an imaging magnification from about 0.8:1 to about 1.2:1, the FLRL 12 is characterized by the following parameters:

rod lens thickness (RLT)=1 cm-2 cm $D_{WKG}$~0.5 cm-2 cm focal length (FCL) ~0.5 cm-2 cm $D_{IMG}$=2 cm-4 cm Comparing the above $D_{IMG}$ of 2 cm-4 cm with the Imaging Distance of 10 cm-30 cm of FIG. A shows that the present invention LICIS 1 with a magnification factor of about 1:1 can be a lot more compactly packaged than the prior art camera image scanner configuration with a tiny magnification factor of 1:72 to 1:18. Secondly, as the focusing optical path 93 of the present invention LICIS 1 can be seen to be dominated by paraxial rays, the previously mentioned need of f-θ compensation and cosine-law fall off of the imaging light intensity toward the edge of the object plane 92 have both become insignificant resulting in a correspondingly improved imaging quality here. Thirdly, the single-camera configuration here has avoided numerous complications associated with the prior art multiple line camera system of FIG. C as well. Fourthly, under the 1:1 imaging system the required FLIS 5 spatial resolution only needs to be about the same as the pixel line image (PLI) 109. Whereas, in a prior art 1:72 imaging system the required CCD Image Sensor spatial resolution would have to be about 72 times higher than the original Object Image.

Figure 3A:
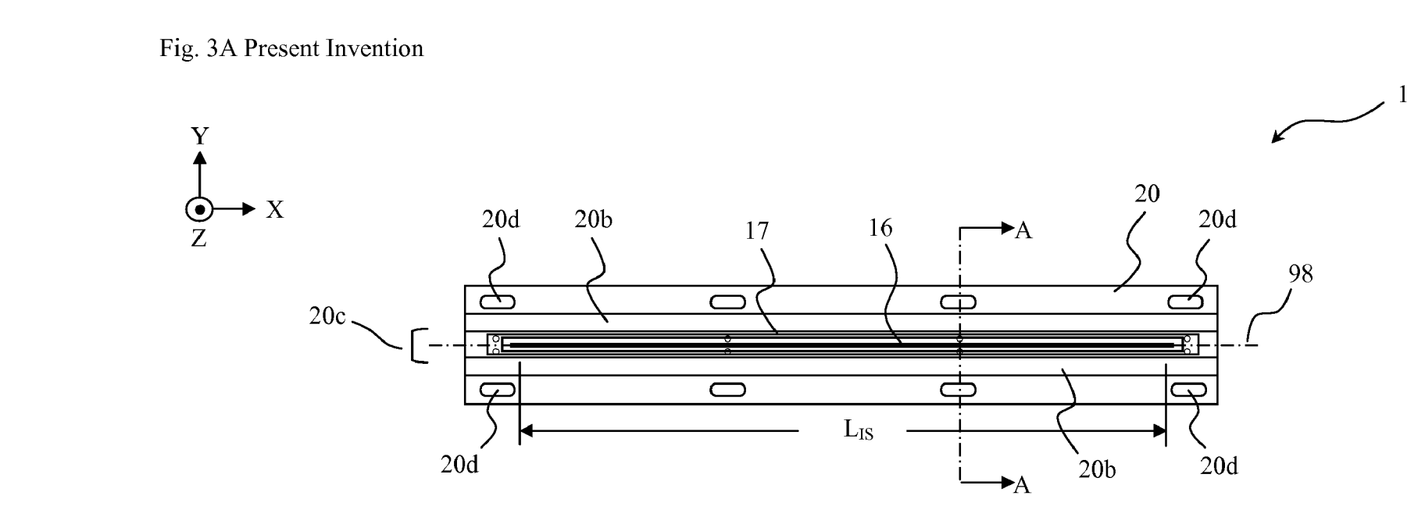
FIG. 3A through FIG. 3C illustrate top, bottom and cross sectional views of the long-length industry camera image sensor (LICIS)
Figure 3B:
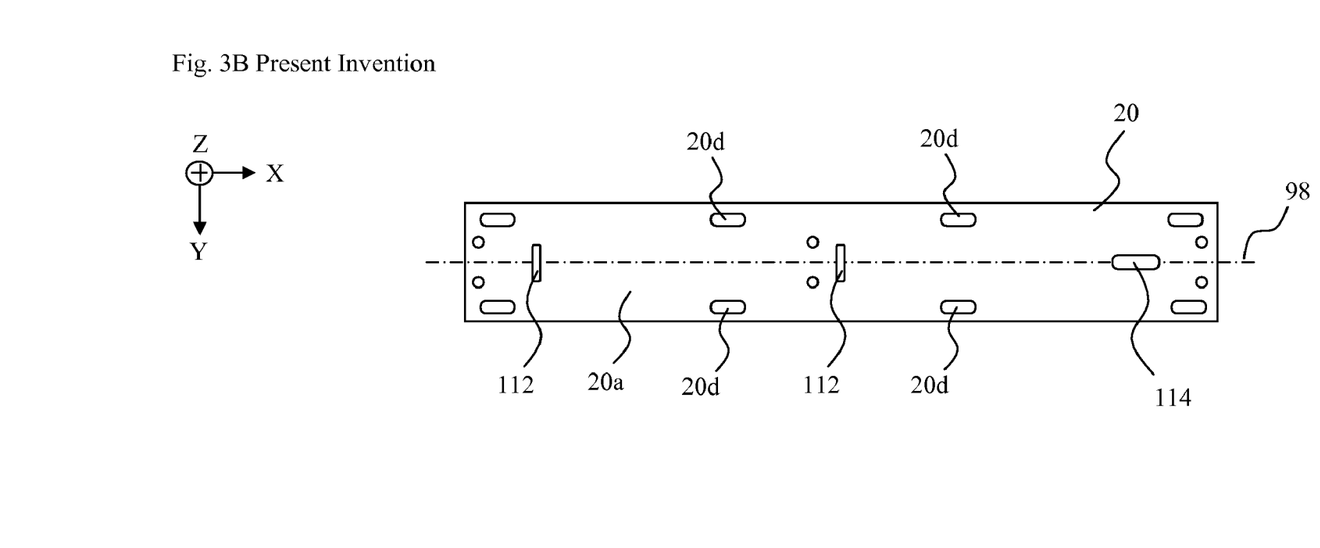
Figure 3C:
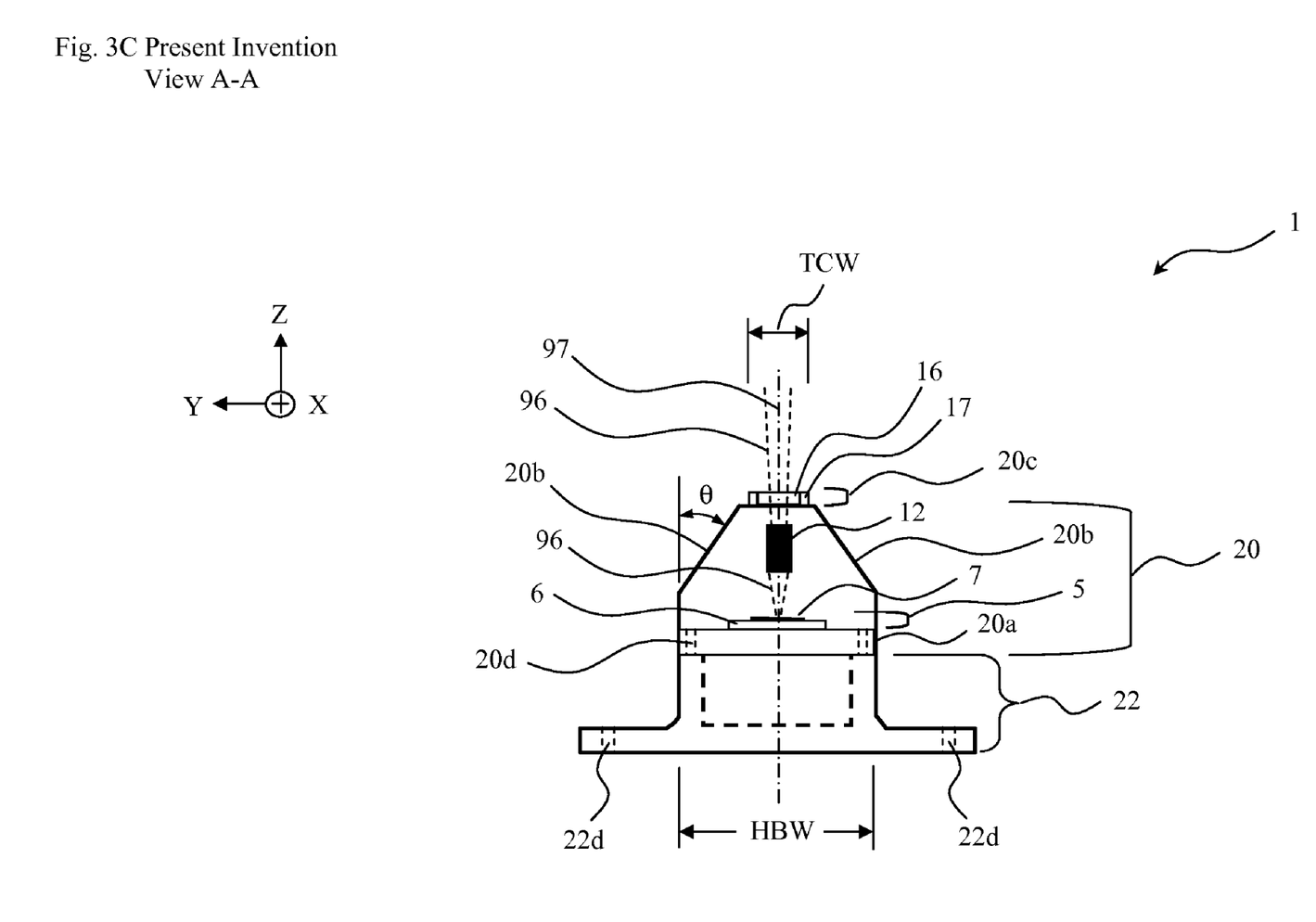

FIG. 3A and FIG. 3B respectively illustrates top and bottom views of the LICIS 1. FIG. 3C illustrates a cross sectional view, along section A-A of FIG. 3A, of the LICIS 1 with an optionally added strutted base bracket 22. The FLIS 5 includes a multi-segment stitched sensor base board (SSBB) 6 seating numerous linearly stitched linear sensor integrated circuits LSIC 7, to be presently described in more detail.

The LICIS 1 has a structured housing 20 for enclosing the FLIS 5 and the FLRL 12 and affixing them with respect to each other. The structured housing 20 has:

A housing base 20a lying in the X-Y plane for seating the FLIS 5. A number of line image signal connectors (LISC) 112 and a power and control connector 114 are provided at the housing base 20a for interfacing and powering the FLIH 1 in its application environment.

Two housing side walls 20b plus a top cover 20c running along the X-axis for enclosing the FLIS 5 and the FLRL 12. The top cover 20c has a transparent central portion for passing through imaging lights 96 near an optical imaging axis 97 along the Z-direction and reaching the FLRL 12. Thus, running through the center of the top cover 20c in the X-direction is an image scan line 98 of the LICIS 1. The transparent central portion has a cover glass 16 held in place by a cover glass holder 17. Notice the top cover width TCW is narrower than the housing base width HBW and, correspondingly, the two housing side walls 20b are tapered toward the top cover 20c with a taper angle θ and this will be presently explained.

Although optional, for the purpose of external mounting in an application environment, the LICIS 1 can include a strutted base bracket 22 having numerous mounting holes 22d. Mounting holes 20d are provided on the structured housing 20 for attaching it to the strutted base bracket 22.

Figure 4A:
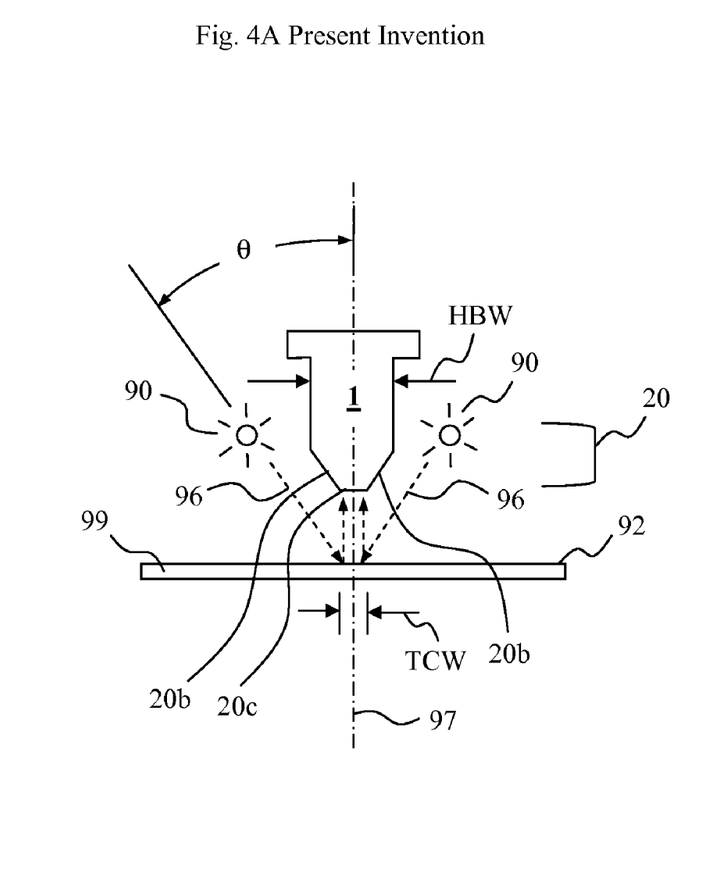
FIG. 4A and FIG. 4B illustrate the application of the long-length industry camera image sensor (LICIS) in a reflective and a transmissive inspection mode.
Figure 4B:
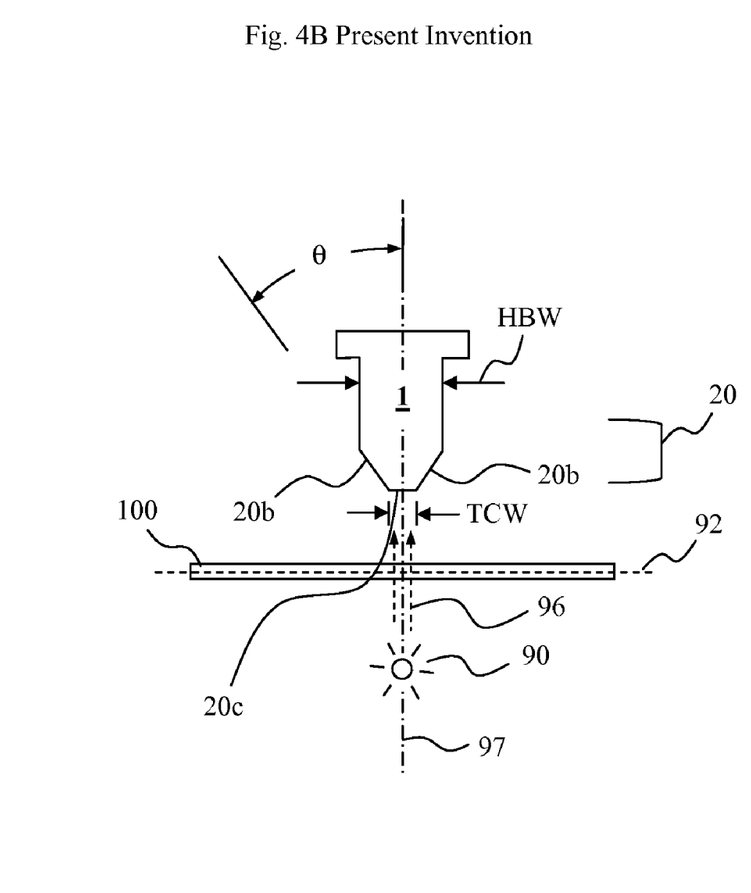

FIG. 4A and FIG. 4B illustrate the application of the LICIS 1 in a reflective (FIG. 4A) and a transmissive (FIG. 4B) inspection mode. Thus, under the reflective mode of FIG. 4A, illumination sources 90 and the FLIH 1 are placed at the same side of a reflective object 99. Whereas, under the transmissive mode of FIG. 4B, illumination source 90 and the LICIS 1 are placed at the opposite sides of a transmissive object 100. Hence, in the reflective mode, to prevent the structured housing 20 from significantly blocking imaging lights 96 travelling from illumination sources 90 near the housing base 20a to an object plane 92 of the reflective object 99, the two housing side walls 20b are tapered toward the top cover 20c with a taper angle θ from the optical imaging axis 97. On the other hand, with the illumination source 90 and the LICIS 1 placed at the opposite sides of the transmissive object 100 under transmissive mode, the tapering of two housing side walls 20b becomes unimportant.

FIG. 5A through FIG. 5D illustrate the mechanical makeup of the multi-segment SSBB 6 of the LICIS 1 for photoelectrically sensing the ILI 102. As mentioned before in FIG. 3C, the SSBB 6 seats numerous linearly stitched linear sensor integrated circuits LSIC 7. More specifically, the SSBB 6 has a number of linearly stitched sensor board segment $SBS_1$ 6A, sensor board segment $SBS_2$ 6B, sensor board segment $SBS_3$ 6C, ..., sensor board segment $SBS_M$ 6M where M>=1. Thus, each SBS converts an incident line image segment of the ILI 102 into a corresponding line-segment image signal of the LIS 110 (FIG. 1). Examples are: sensor board segment $SBS_1$ 6A converts incident line image segment $ILI_1$ 102A into line-segment image signal $(LSIS_1)$ 104A, sensor board segment $SBS_2$ 6B converts incident line image segment $ILI_2$ 102B into line-segment image signal $(LSIS_2)$ 104B, sensor board segment $SBS_3$ 6C converts incident line image segment $ILI_3$ 102C into line-segment image signal $(LSIS_3)$ 104C, ..., sensor board segment $SBS_M$ 6M converts incident line image segment $ILI_M$ 102M into line-segment image signal $(LSIS_M)$ 104M. In turn, an enlarged representative sensor board segment $SBS_3$ 6C is illustrated to have a base board $BB_3$ 7C with numerous stitched linear sensor integrated circuit LSIC 7C1, linear sensor integrated circuit LSIC 7C2, linear sensor integrated circuit LSIC 7C3, ..., linear sensor integrated circuit LSIC 7CN located atop. Thus, each linear sensor integrated circuit LSIC (7C1, 7C2, ... ) would further convert an incident line image segment (1031, 1032, ...) of the incident line image segment $ILI_3$ 102C into a corresponding line-segment image signal. The reason for the just described scheme of photoelectrical conversion via stitching with numerous LSICs as building blocks is that the length of each LSIC is, under state of the art semiconductor chip manufacture technology, limited to a few inches whereas the required length $L_{IS}$ of the full-width linear image sensor (FLIS) 5 can be easily as large as 36 to 72 inches. In a preferred embodiment the base board can be made of a printed circuit board (PCB) or a ceramic circuit substrate and the LSIC can be made of a linear CMOS sensor integrated circuit.

Figure 5A:
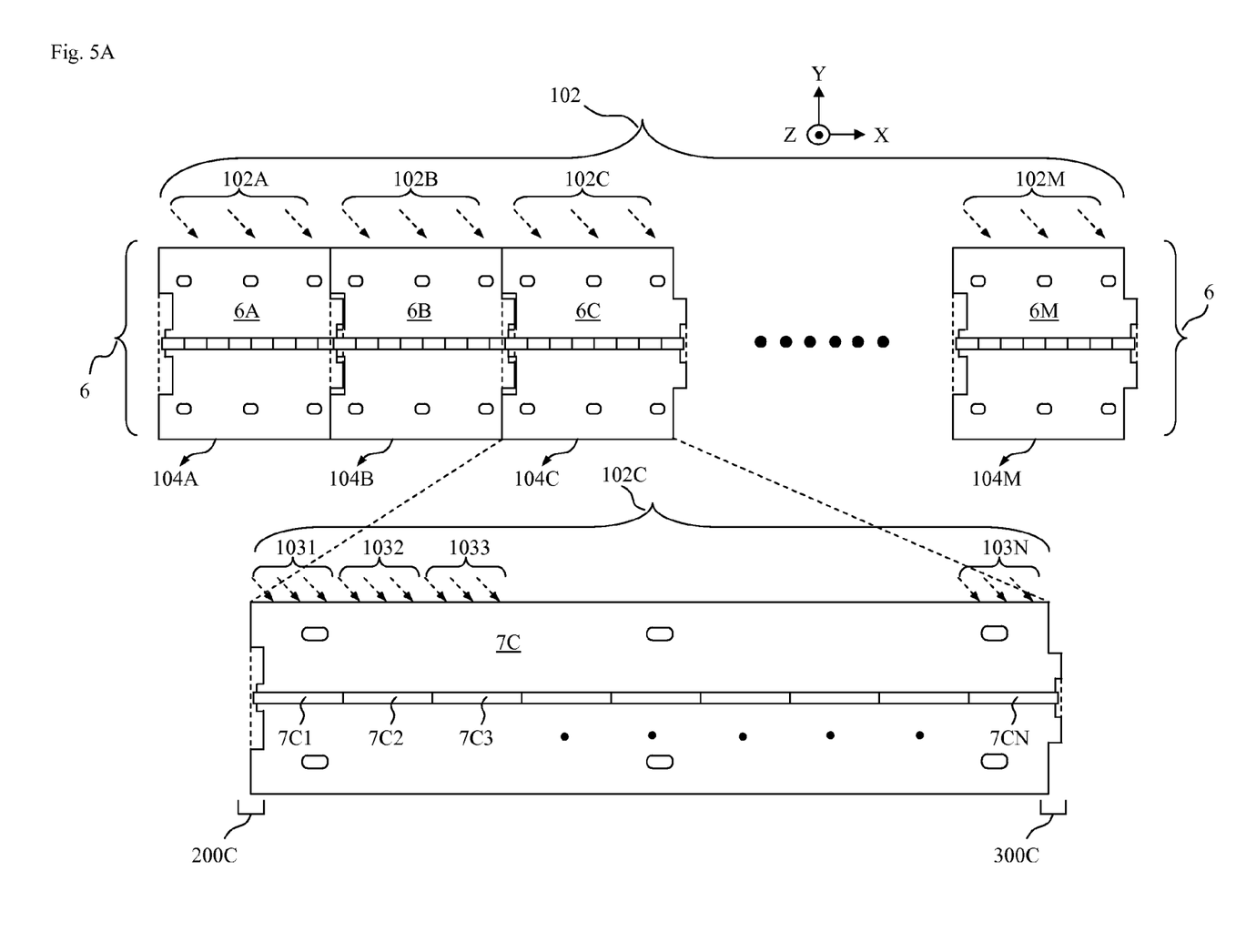
FIG. 5A through FIG. 5D illustrate the mechanical makeup of a stitched sensor base board (SSBB) of the long-length industry camera image sensor (LICIS) for photoelectrically sensing an incident line image (ILI).
Figure 5B:
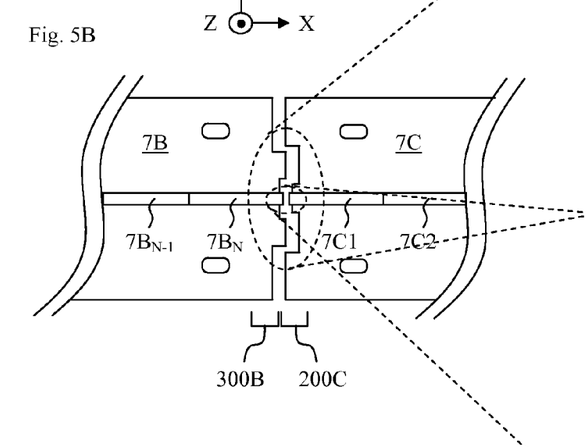
Figure 5C:
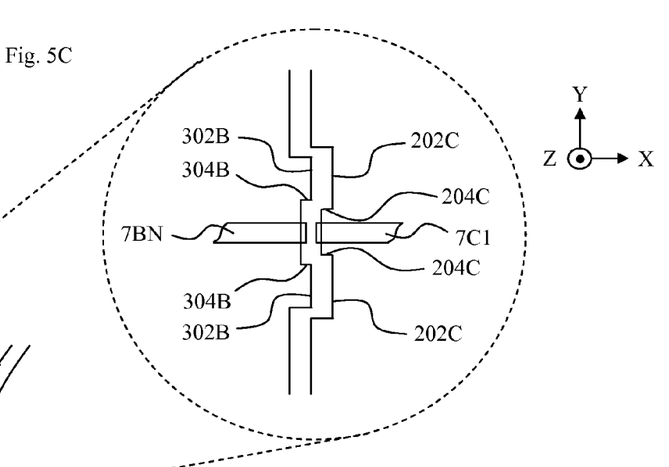
Figure 5D:
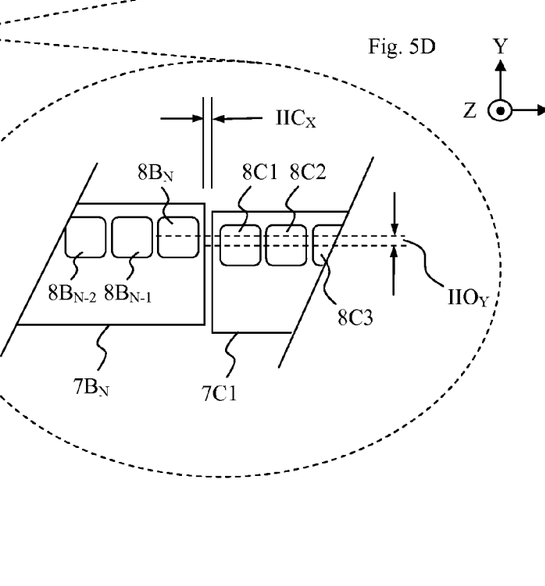

Notice each base board (7B, 7C, etc.) has a left-end anti-bumping profile 200C and a right-end anti-bumping profile 300C with enlarged views shown in FIG. 5B through FIG. 5D. The rightmost LSIC elements atop base board $BB_2$ 7B are LSIC 7BN-1 and LSIC 7BN whereas the leftmost LSIC elements atop base board $BB_3$ 7C are LSIC 7C1 and LSIC 7C2. The right-end anti-bumping profile 300B is shaped with protruded anti-bumping edge (PABE) 302B and recessed offset control edge (ROCE) 304B. Correspondingly, the left-end anti-bumping profile 200C is shaped with recessed anti-bumping edge (RABE) 202C and protruded offset control edge (POCE) 204C respectively engaging with the protruded anti-bumping edge (PABE) 302B and the recessed offset control edge (ROCE) 304B to prevent the LSIC 7BN and the LSIC 7C1 from bumping thus damaging each other along the X-direction during assembly and from displacing from each other with an otherwise excessive amount of offset along the Y-direction. The rightmost photoelectric sensor pixels of the LSIC 7BN are labeled as 8BN-2, 8BN-1 and 8BN whereas the leftmost photoelectric sensor pixels of the LSIC 7C1 are labeled as 8C1 and 8C2 displaced from (8BN-2, 8BN-1, 8BN) with a Y-direction inter-IC offset ($IIO_Y$) causing an inter-sensor board segment (inter-SBS) image offset that should be minimized for high image quality. Hence, upon engagement of the ROCEs 304B with the POCEs 204C the Y-direction inter-IC offset ($IIO_Y$) is guaranteed not to exceed a pre-determined maximum value. Similarly, the center-to-center spacing between sensor pixel 8BN and sensor pixel 8C1 should be made as close to the on-chip, precision center-to-center inter-sensor pixel spacings (for example, between sensor pixels 8BN-1 and 8BN and likewise between sensor pixels 8C1 and 8C2). Hence, upon engagement of the PABEs 302B with the RABEs 202C the X-direction inter-IC clearance ($IIC_X$) is guaranteed not to fall below another pre-determined minimum value for acceptable uniformity of inter-sensor pixel spacing. In a more specific embodiment, the $IIC_X$ can be controlled to within a range from about 10 micron to about 30 micron while the $IIO_Y$ can be controlled to within a range from about 0 micron to about 30 micron. An advantage related to the use of the as described anti-bumping profiles (300B, 200C, etc.) between neighboring SBSs is the prevention of excessive buildup of inter-SBS misalignment due to environmental variations such as temperature and humidity. By now it should become clear to those skilled in the art that a large number of variations of the specifically illustrated anti-bumping profiles (302B, 304B, 202C, 204C), including profiles deviated from both X- and Y-direction, can be used instead to limit the inter-SBS misalignment as well.

A full width line image sensing head long-length industry camera image sensor is proposed for converting a pixel line image into a corresponding line image signal with an imaging magnification factor of about 1:1. Throughout the description and drawings, numerous exemplary embodiments were given with reference to specific configurations. It will be appreciated by those of ordinary skill in the art that the present invention can be embodied in numerous other specific forms and those of ordinary skill in the art would be able to practice such other embodiments without undue experimentation. The scope of the present invention, for the purpose of the present patent document, is hence not limited merely to the specific exemplary embodiments of the foregoing description, but rather is indicated by the following claims. Any and all modifications that come within the meaning and range of equivalents within the claims are intended to be considered as being embraced within the spirit and scope of the present invention.

What is claimed is:

1. A long-length industry camera image sensor (LICIS) for flat surface inspection application, the LICIS functions to, expressed in an X-Y-Z Cartesian coordinate system, photoelectrically convert a pixel line image (PLI) of length $L_{PL}$ oriented along the X-direction into a corresponding line image signal (LIS), the LICIS comprises:
   a) a full-width linear image sensor (FLIS) of length $L_{IS}$ oriented along the X-direction and displaced from the PLI along the Z-direction by an imaging distance $D_{IMG}$, wherein $L_{IS}$ is about equal to $L_{PL}$, for converting an incident line image (ILI) onto top surface of the FLIS into said corresponding LIS; the FLIS comprises a multi-segment stitched sensor base board (SSBB) having a plurality of linearly stitched sensor board segments $SBS_j$, j=(1, 2, . . . , M) where M>=1 with each $SBS_j$ converting an incident line image segment ($ILI_j$) of the ILI into a corresponding line image signal segment ($LIS_j$) of the LIS; wherein:
   a1) each $SBS_j$ further comprises:
   a base board ($BB_j$); and a plurality of linearly stitched linear sensor integrated circuit $LSIC_{jk}$, k=(1, 2, . . . , N) located atop the base board where N>=1 with each $LSIC_{jk}$ converting an incident line image segment ($ILI_{jk}$) of the $ILI_j$ into a corresponding line image signal segment ($LIS_{jk}$) of the $LIS_j$; and
   a2) along the X-direction, each $BB_j$ further comprises a left-end anti-bumping profile and a right-end anti-bumping profile such that, when the $BB_j$ and $BB_{j+1}$ are stitched together, the right-end anti-bumping profile of $BB_j$, will engage the left-end anti-bumping profile of $BB_{j+1}$ and accordingly guaranteeing:
   a minimum X-direction inter-IC clearance ($IIC_X$) between $LSIC_{jN}$ and $LSIC_{j+1,1}$; and
   a maximum Y-direction inter-IC offset ($IIO_Y$) between $LSIC_{jN}$ and $LSIC_{j+1,1}$; and
   b) a full-width linear rod lens (FLRL) of length $L_{RL}$ oriented along the X-direction and displaced from the PLI in the Z-direction by a working distance $D_{WKG}$ with $D_{WKG} < D_{IMG}$ hence said FLRL being located intervening to the PLI and the FLIS, and wherein $L_{RL}$ is about equal to $L_{PL}$ and said $D_{WKG}$ is further selected with respect to $D_{IMG}$ such that the PLI gets focused by the FLRL into the ILI at the FLIS top surface with an imaging magnification factor of about 1:1; whereby
the LICIS, with no built-in interior light source, senses a PLI of length $L_{PL}$ longer than that of a single sensor board segment via the combination of:
   inter-linear sensor integrated circuit image stitching on each base board $BB_j$; and
   inter-base board image stitching on the multi-segment stitched sensor base board SSBB.

2. The LICIS of claim 1 wherein said imaging magnification factor is from about 0.8:1 to about 1.2:1.

3. The LICIS of claim 1 wherein each $LSIC_{jk}$ is made of a linear CMOS sensor integrated circuit.

4. The LICIS of claim 1 wherein said $IIC_X$ is from about 10 micron to about 30 micron.

5. The LICIS of claim 1 wherein said $IIO_Y$ is from about 0 micron to about 30 micron.

6. The LICIS of claim 1 further comprises, for enclosing the FLIS and the FLRL while affixing them with respect to each other, a structured housing having:
   a housing base lying in the X-Y plane for seating the FLIS; and
   two housing side walls plus a top cover running along the X-axis for enclosing the FLIS and the FLRL.

7. The LICIS of claim 6 wherein the top cover further comprises a transparent central portion for passing through imaging lights near an optical imaging axis along the Z-direction and reaching the FLRL.

8. The LICIS of claim 7 wherein:
   the width of the top cover along the Y-direction is, while avoiding significant blockage of the imaging lights therethrough, minimized to become narrower than a corresponding width of the housing base; and
   correspondingly, the upper portions of both housing side walls are tapered from the housing base toward the top cover so as to minimize the blockage of lateral illumination lights originated near the housing base and aiming at a reflective surface being imaged above the FLIH.

9. The LICIS of claim 1 wherein said $D_{WKG}$ is from about 0.5 cm to about 2 cm.

* * * * *